United States Patent [19]

Chan

[11] Patent Number: 4,481,956
[45] Date of Patent: Nov. 13, 1984

[54] SMOKING COMPOSITIONS

[75] Inventor: Woontung G. Chan, Richmond, Va.

[73] Assignee: Philip Morris Incorporated, New York, N.Y.

[21] Appl. No.: 417,271

[22] Filed: Sep. 13, 1982

[51] Int. Cl.$^3$ .......................... A24B 3/12; A24B 15/32
[52] U.S. Cl. .................................................. 131/276
[58] Field of Search ............... 131/275, 276, 277, 278, 131/279

[56] References Cited

U.S. PATENT DOCUMENTS

| | | | |
|---|---|---|---|
| 3,313,307 | 4/1967 | Rohde | 131/276 |
| 3,403,686 | 10/1968 | Kilburn et al. | 131/276 |
| 3,644,613 | 2/1972 | Moeller et al. | 424/49 |
| 4,200,659 | 4/1980 | Willis et al. | 426/534 |

FOREIGN PATENT DOCUMENTS 1589916   5/1981   United Kingdom .

OTHER PUBLICATIONS

W. J. Bailey et al., J. Org. Chem. 22, 1189–1192 (1957).

*Primary Examiner*—V. Millin
*Attorney, Agent, or Firm*—Arthur I. Palmer; James E. Schardt

[57] ABSTRACT

A non-volatile source of ketone to flavor tobacco smoke is provided by a β-ketocarboxylic acid ester of a sugar or related compound. The ester is applied to the smoking material and remains in place until the burning coal releases the ketone.

3 Claims, No Drawings

SMOKING COMPOSITIONS

BACKGROUND OF THE INVENTION

This invention relates to an improved smoking tobacco product and the method of making the same, and more particularly to an improved smoking tobacco product having incorporated therein aroma and flavor-producing additives which improve the smoking characteristics thereof.

There has been continuing interest in using organic material which can function as flavoring agents for modifying or improving the flavor and aroma of tobaccos, foodstuffs, beverages and other such consumer products.

It is been established that ketones are natural components of tobacco smoke, and that they most probably are contributors to tobacco smoke flavor. Further, it has been disclosed in the patent literature that addition of ketones to tobacco results in an improvement in the flavor of smoking compositions as perceived by test panels.

U.S. Pat. No. 3,174,485 discloses the addition of p-methylacetophenone to tobacco and food stuffs as a means of providing flavor or flavor enhancement. Other patents which disclose the use of aromatic ketones include U.S. Pat. No. 3,605,760 for 3,5-dialkyl-2-hydroxyacetophenone and U.S. Pat. No. 3,389,706 for 5-methyl-2-acetylfuran.

Aliphatic ketones have also been found to be useful tobacco additives. U.S. Pat. No. 3,174,485 describes the use of geranylacetone and 6-methyl-5-hepten-2-one as tobacco additives, whereas U.S. Pat. No. 4,103,036 discloses 1-(3,3-dimethylcyclohexyl)-4-methylpentanone as a tobacco additive. Canadian Pat. No. 895,916 describes the synthesis of 1-acetyl-3-isopropylcyclopentane and its use to enhance the flavor of tobacco smoke.

Ketoacid esters of menthol were disclosed as tobacco flavorants by Moeller et al in U.S. Pat. No. 3,644,613. Willis discloses diethyl α,β-diacetylsuccinate as a flavorant for tobacco, in U.S. Pat. No. 4,200,659. Esters of ketoalcohols as tobacco flavors were disclosed by Kilburn et al, U.S. Pat. No. 3,403,686.

Sucrose 2,2,4-trimethyl-3-oxovalerate is a beta-ketocarboxylic ester which has been described by Wright in U.S. Pat. No. 3,106,477 and proposed as an extender for cellulose esters in film making and the like.

The present invention provides for the incorporation in tobacco or other smoking material of a compound which will impart flavors to the smoke thereof, which compound is not lost during manufacturing and storage and which compound is readily released when the tobacco is smoked.

It is an objective of this invention to permit the incorporation of a ketone into a tobacco product in a form which will not be lost or altered during subsequent manufacturing steps or during storage of the tobacco product.

It is a further objective of this invention to permit the incorporation of a material in tobacco, which material will release a ketone into the tobacco smoke which results when the tobacco containing said material is smoked.

One of the more specific objects of the present invention is to incorporate ketones in a tobacco product in such a manner that they will not be released prior to the time that the tobacco product is smoked but will be readily and efficiently released as the tobacco product is smoked.

DESCRIPTION OF THE INVENTION

In accordance with the present invention, a β-ketoester derivative of a carbohydrate is incorporated in a smoking product. The β-ketoester derivative of a carbohydrate which may be employed in the present invention may be represented by the following formula:

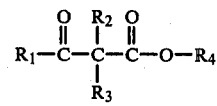

$$R_1-\overset{O}{\underset{\|}{C}}-\overset{R_2}{\underset{R_3}{C}}-\overset{O}{\underset{\|}{C}}-O-R_4 \qquad \text{I}$$

where $R_1$ is an aliphatic or alicyclic alkyl radical having one to 12 carbon atoms, or an aromatic or aralkyl radical with or without substituents on the ring or a heterocyclic radical having four to 10 carbon atoms;

$R_2$ and $R_3$ are each either a hydrogen or an alkyl radical having one to six carbon atoms, or an aromatic radical with or without substituents on the ring or a heterocyclic radical having four to 10 carbon atoms;

$R_2$ and $R_3$ can also be joined together to form a cyclic ring structure; and $R_4$ is a carbohydrate radical or polyhydroxy alkyl radical.

Illustrative of the $R_1$, $R_2$, and $R_3$ substituents in the formula represented above are methyl, propenyl, butyl, pentyl, hexenyl, methoxyethyl, cyclopropyl, cyclobutyl, cyclopentyl, cyclohexyl, furyl, tetrahydrofuryl, phenyl, tolyl, xylyl, benzyl, phenylethyl, hydroxyphenyl, methoxyphenyl, naphthyl, pyridyl, pyridazyl, and the like.

As noted previously, $R_2$ and $R_3$ can be joined together to form an alicyclic group such as cyclopentyl, cyclohexyl, cycloheptyl, and the like.

Illustrative of $R_4$ substituents in the formula represented above are glucose, mannose, galactose, rhamnose, xylose, galactitol, mannitol, glycerol, methyl glucoside, methyl galactoside, phenyl glucoside, and the like; and their isopropylidene, ethylidene, and benzylidene derivatives.

A β-ketoester derivative of a carbohydrate corresponding to the formula represented above is usually solid or a viscous syrup having very low volatility. Under normal smoking conditions, or other comparably intensive localized heating conditions, it pyrolyzes into products, one of which is a ketone having the following general formula:

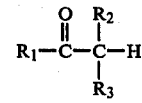

$$R_1-\overset{O}{\underset{\|}{C}}-\overset{R_2}{\underset{R_3}{C}}-H \qquad \text{II}$$

where $R_1$, $R_2$ and $R_3$ are as represented above for structure I.

A detailed study of the mechanism of release of the flavorful ketones II from β-ketoester I, where $R_4$ is ethyl, has been reported (W. J. Bailey and J. J. Daly, Jr., J. Org. Chem., 22, 1189 [1957]). In Scheme I, ethyl acetoacetate (I, $R_1=CH_3$, $R_2=R_3=H$, $R_4=C_2H_5$) first undergoes 1,2-elimination at the ethyl ester portion to generate acetoacetic acid (I, $R_1=CH_3$, $R_2=R_3=R_4=H$) and ethene. This is the rate determining step and requires high temperature. (The study was conducted at 460°–560° C.). The acetoacetic acid then undergoes spontaneous decarboxylation to generate the ketone, in this case, acetone (II, $R_1=CH_3$, $R_2=R_3=H$).

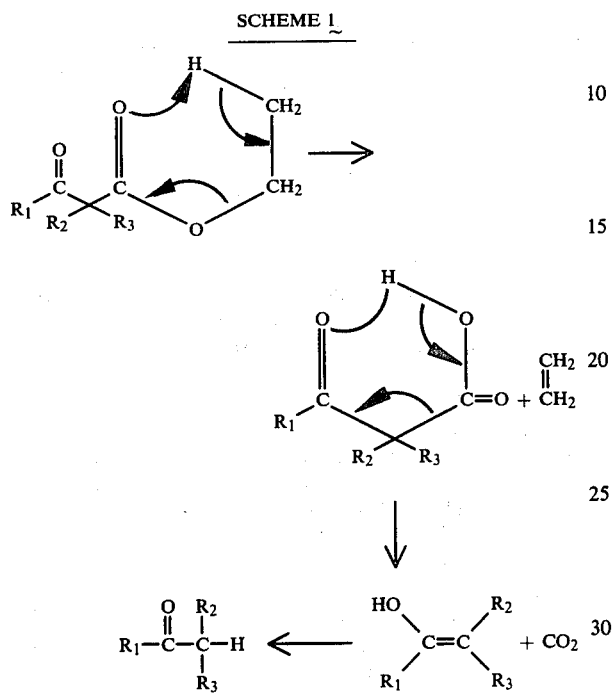

When $R_4$ is a radical derived from a carbohydrate, or polyhydroxy compound, the release of II from I follows the same mechanism, that is, from the ketoester (I, $R_4$=carbohydrate or polyhydroxy compound) to the ketoacid (I $R_4$=H), then to the ketone (II). (Scheme 2, where R', R" and R''' are taken together to form the carbohydrate or polyhydroxy radical.)

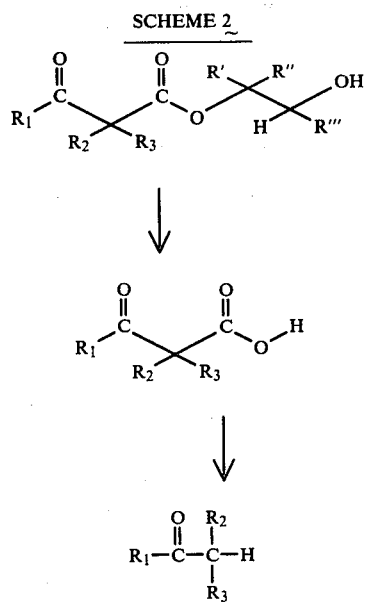

The major advantage of using a carbohydrate or a polyhydroxy radical instead of a simple alkyl radical for $R_4$ is that pyrolysis takes place at a lower temperature.

The following three carbohydrate derivatives, 1,2:5,6-di-O-isopropylidene-3-O-(3-p-methylphenyl-3-oxo)propionyl-α-D-glucofuranose, 1,2-O-isopropylidene-3-O-(3-p-methylphenyl-3-oxo)propionyl-α-D-glucofuranose and 3-O-(3-p-methylphenyl-3-oxo)propionyl-D-glucopyranose, were pyrolysed in a 250° C. oil bath for 5 minutes to produce a 31%, 29% and 67% yield of p-methylacetophenone respectively, whereas ethyl 3-(p-methylphenyl)-3-oxopropionate remained unchanged.

Another advantage of additives of the present invention over a simple alkyl β-ketoester is that the alkyl esters have a greater tendency to distill. For example, ethyl 3-(p-methylphenyl)-3-oxopropionate has a boiling point of 138°–140°/1.5 mm whereas none of the three carbohydrate derivatives named above can be distilled without significant decomposition.

PREPARATION OF β-KETOESTERS OF CARBOHYDRATE DERIVATIVES

One method of preparing the carbohydrate β-ketoester compounds of the present invention is by the reaction of an alkanoate derivative with a carbonyl derivative:

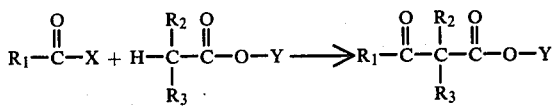

where
X=Cl, Br or alkoxy radical
Y=carbohydrate or polyhydroxy radical with most of its hydroxyl groups protected;
$R_1$, $R_2$, $R_3$, and $R_4$ are as previously defined.

The reaction is conducted in the presence of a strong base such as phenyllithium, lithium diisopropylamide, lithium tetramethylpiperidene (LTMP), or alkali metal hydride. The conversion of Y into $R_4$ can be carried out in a number of different ways depending on the nature of protecting groups used, e.g. hydrogenation for benzyl ethers, fluoride ion promoted hydrolysis for silyl ethers, and careful acidic hydrolysis for isopropylidene, benzylidene and ethylidene protecting groups. The following synthesis of 3-O-(3-methylphenyl)-3-oxopropionyl-D-glucopyranose is illustrative.

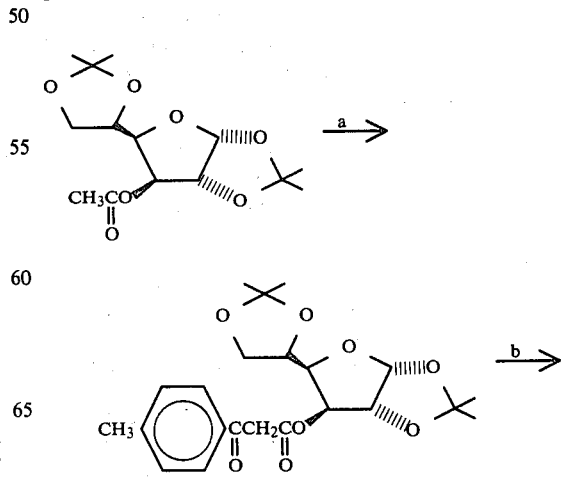

-continued

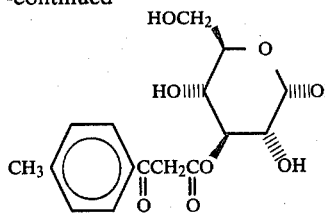

(a) LTMP/THF; p-methylbenzoyl chloride/THF
(b) 90% CF$_3$CO$_2$H

Another method of preparing the carbohydrate β-ketoester compound is by the reaction of an alkanoate derivative with an aldehyde to give a carbohydrate β-hydroxyester compound followed by oxidation of the hydroxyl group to the ketone.

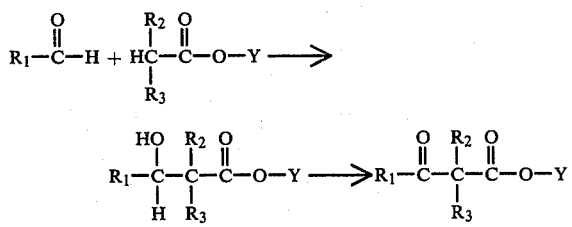

The first reaction is again conducted in the presence of a strong base as in the previous method. The second reaction is carried out in the presence of such oxidizing agents as Jones reagent, pyridinium dichromate, Collins reagent, dimethyl sulfoxide/oxalyl chloride and the like. Conversion of Y into R$_4$ would be as previously indicated.

The preparation and use of these esters for ketone release are illustrated by the following Examples which are not intended to limit the invention.

EXAMPLE I 1,2:5,6-Di-O-isopropylidene-3-O-acetyl-α-D-glucofuranose(2)

A solution of 13 g 1,2:5,6-di-O-isopropylidene-α-D-glucofuranose (0.05 mole) and 20 g pyridine (0.25 mole) in 100 mL of tetrahydrofuran (THF) was cooled to $-5°$ C. A solution of 5 g acetyl chloride (0.06 mole) was added dropwise at this temperature over 20 min. The mixture was allowed to warm to room temperature over 1 hour and stirred at this temperature for 2 days. The mixture was poured into a chilled aqueous ammonia solution (10 mL conc. NH$_4$OH, 100 mL water and 20 g ice). Methylene chloride (100 mL) was added and the layers were separated. The aqueous layer was extracted twice with 100 mL of methylene chloride and the combined organic layer washed with 80 mL each of saturated aqueous solutions of ammonium chloride, sodium bicarbonate and sodium chloride. The methylene chloride solution was then dried over magnesium sulfate. After removal of solvent by rotary evaporation under vacuum, the crude solid was recrystallized from hexane to give 14.8 g of product (97% yield), m.p. 60° C. (lit. m.p. 59°-60° C.).

1,2:5,6-Di-O-isopropylidene-3-O-(3-p-methylphenyl-3-oxo)propionyl-α-D-glucofuranose (3)

A solution of lithium tetramethylpiperidine in tetrahydrofuran (THF) was prepared from 4.7 g (33 mole) of tetramethylpiperidine and 13.2 mL of a 2.5M solution of n-butyllithium. The solution was cooled to $-70°$ C. and a solution of 5 g (17 mmole) 1,2:5,6-di-O-isopropylidene-3-O-acetyl-α-D-glucofuranose (2) in 20 mL THF was added. After stirring for 10 minutes, a solution of 2.56 g (17 mmole) of p-toluoyl chloride in 5 mL of THF was added. After stirring for an additional 10 minutes, a 10 mL portion of 20% hydrochloric acid was added and the mixture allowed to warm to room temperature. The layers were separated and the organic layer was washed twice with 50 mL of water. The combined aqueous layer was back extracted once with 150 mL methylene chloride. The combined organic layers were then washed with saturated solutions of sodium bicarbonate and sodium chloride and then dried over magnesium sulfate. After removal of solvent by rotary evaporation under vacuum, the crude solid was recrystallized from hexane to give 4.8 g of product (69% yield), m.p. 95.5°-97° C.

EXAMPLE II 1,2-O-Isopropylidene-3-O-(3-p-methylphenyl-3-oxo)-propionyl-α-D-glucofuranose (4)

A mixture of 2 g of 3 (4.8 mmole), 10 mL of water, 40 mL of tetrahydrofuran and 3 mL of concentrated hydrochloric acid was heated at 45° under nitrogen with stirring for 8 hours. After cooling to room temperature, the mixture was saturated with sodium carbonate. The layers were separated and the aqueous layer was extracted twice with 25 mL of ether. The combined organic layers were washed twice with 25 mL of saturated sodium chloride and then dried over magnesium sulfate. After removal of solvent by rotary evaporation, the crude solid was recrystallized from ethyl acetate to give 1.06 g of product (60% yield) m.p. 129.5°-131° C.

EXAMPLE III

3-O-(3-p-Methylphenyl-3-oxo)propionyl-D-glucopyranose (5)

A solution of 9 mL trifluoroacetic acid and 1 mL of water was cooled in an ice bath. A 2 g sample of 3 (4.8 mmole) was added and the mixture was allowed to warm to room temperature over 1.5 hours. Most of the acid and water were removed by rotary evaporation. The residue was dissolved in 10 mL of ethanol and the residual acid was neutralized with 1 g of sodium bicarbonate. The inorganic salt was filtered off and the filtrate was evaporated to dryness on a rotary evaporator. The crude solid was recrystallized from ethanol/ethyl acetate to give 0.95 g of product (60% yield), m.p. 170°-171° C.

EXAMPLE IV

Pyrolysis of ketone-release compounds

About 10 mg each of a sample of 3, 4 and 5 was placed in one of 3 nmr tubes. The tubes were then placed into a 250°±1° C. oil bath for 5 minutes. After the tubes were cooled to room temperature, 300 μL of deuterated chloroform was added into each tube and a 3 μL aliquot of each solution was analyzed by gas chromatography. A standard solution of 51.1 mg of p-methylacetophenone (6) in 5 mL of deuterated chloroform was prepared and a 3 μl aliquot was injected into the gas chromatograph. The following results were obtained.

| | Wt. of Material injected (µg) | Area | Wt. of Product µg | Theoretical Yield (µg) | Yield |
|---|---|---|---|---|---|
| 3 | 97 | 2.23 | 9.7 | 30.9 | 31% |
| 4 | 95 | 2.25 | 9.7 | 33.5 | 29% |
| 5 | 109 | 6.70 | 29.0 | 43.0 | 67% |
| 6 | 30.7 | 7.08 | | | |

The amount of unchanged material in each case was not determined.

EXAMPLE V

Pyrolysis of ketone release compound in a helium flow system

About 1 mg sample was accurately weighed into a porcelain boat. The boat was then placed in a horizontal quartz tube surrounded by a furnace held at a known temperature. A stream of helium (50 cc/min) flowed through the quartz tube to flush the pyrolysate into the injector port of a gas chromatograph. The amount of ketone formed was analyzed against an external standard. The results for 3, 4, and 5 are shown in FIG. 1.

I claim:

1. A smoking product having added thereto a β-ketocarboxylic acid ester of a carbohydrate or of an alkyl polyol.

2. The smoking product of claim 1 wherein the added ester is that of a sugar or sugar glycoside.

3. The smoking product of claim 1 wherein the beta-ketocarboxylic acid of the added ester is p-methylbenzoylacetic acid.

* * * * *